United States Patent
Deych et al.

(10) Patent No.: US 7,431,500 B2
(45) Date of Patent: Oct. 7, 2008

(54) DYNAMIC EXPOSURE CONTROL IN RADIOGRAPHY

(75) Inventors: Ruvin Deych, Brookline, MA (US); Bernard M. Gordon, Manchester-by-the-Sea, MA (US); Oscar Khutoryansky, Newton, MA (US)

(73) Assignee: Analogic Corporation, Peabody, MA (US)

( * ) Notice: Subject to any disclaimer, the term of this patent is extended or adjusted under 35 U.S.C. 154(b) by 0 days.

(21) Appl. No.: 10/814,992

(22) Filed: Mar. 31, 2004

(65) Prior Publication Data

US 2005/0069086 A1   Mar. 31, 2005

Related U.S. Application Data

(60) Provisional application No. 60/527,236, filed on Dec. 5, 2003, provisional application No. 60/459,480, filed on Apr. 1, 2003.

(51) Int. Cl.
*G01D 18/00* (2006.01)
*G01N 23/083* (2006.01)
*H05G 1/64* (2006.01)
*H05G 1/32* (2006.01)

(52) U.S. Cl. ............ 378/207; 378/37; 378/62; 378/98.7; 378/98.8; 378/111; 378/112

(58) Field of Classification Search ............ 378/16, 378/62, 95–97, 98.7, 98.9, 98.11, 108–112, 378/207, 98.8
See application file for complete search history.

(56) References Cited

U.S. PATENT DOCUMENTS

| | | | | |
|---|---|---|---|---|
| 4,686,695 A | * | 8/1987 | Macovski | 378/146 |
| 4,748,649 A | * | 5/1988 | Griesmer et al. | 378/97 |
| 4,797,905 A | * | 1/1989 | Ochmann et al. | 378/108 |
| 5,150,393 A | * | 9/1992 | Aichinger et al. | 378/37 |
| 5,388,139 A | * | 2/1995 | Beland | 378/112 |
| 5,446,780 A | * | 8/1995 | Aichinger et al. | 378/204 |
| 5,574,764 A | * | 11/1996 | Granfors et al. | 378/98.7 |
| 6,047,042 A | * | 4/2000 | Khutoryansky et al. | 378/62 |
| 6,151,383 A | * | 11/2000 | Xue et al. | 378/108 |
| 6,192,105 B1 | * | 2/2001 | Hunter et al. | 378/108 |
| 6,208,710 B1 | * | 3/2001 | Nagai | 378/108 |
| 6,243,440 B1 | * | 6/2001 | Oikawa et al. | 378/98.8 |
| 6,327,336 B1 | * | 12/2001 | Gingold et al. | 378/98.7 |
| 6,330,302 B1 | * | 12/2001 | Joosten | 378/98.12 |
| 6,442,238 B2 | * | 8/2002 | Meulenbrugge | 378/98.8 |
| 6,459,765 B1 | * | 10/2002 | Ganin et al. | 378/108 |
| 6,501,819 B2 | * | 12/2002 | Unger et al. | 378/5 |
| 6,516,098 B2 | * | 2/2003 | Nonaka | 382/274 |

(Continued)

*Primary Examiner*—Allen C. Ho
(74) *Attorney, Agent, or Firm*—McDermott Will & Emery, LLP (57) ABSTRACT

A method and system is presented in radiography for optimizing image quality of an object (e.g. an anatomical region of a patient), while minimizing the radiation dose to the patient. X-ray exposure parameters, such as operating voltage (kVp), operating current (mA), focal spot size, and soft x-ray filter combination, are dynamically controlled during the x-ray exposure. During at least two different sampling intervals and at two different kVp levels, x-rays are passed through the object, and detected by sensors located between the object and the image plane. After the last sampling interval, the sensor output signals and the measured thickness of the object are used to evaluate the optimal settings for the x-ray exposure parameters. The x-ray exposure parameters are set to these optimal settings for the remainder of the exposure period.

17 Claims, 5 Drawing Sheets

U.S. PATENT DOCUMENTS

| | | | |
|---|---|---|---|
| 6,594,337 B1 | 7/2003 | Silver et al. | 378/85 |
| 6,594,339 B1 * | 7/2003 | Alving et al. | 378/98.7 |
| 6,618,090 B1 | 9/2003 | Kidono et al. | 348/362 |
| 6,754,307 B2 | 6/2004 | Brendler et al. | 378/108 |
| 6,768,784 B1 * | 7/2004 | Green et al. | 378/62 |
| 6,920,201 B2 * | 7/2005 | Maack et al. | 378/116 |
| 6,944,266 B2 * | 9/2005 | Yamazaki et al. | 378/98.7 |

* cited by examiner

TABLE 1

Simulated Effective Linear Attenuation Coefficient of Breast Tissue in cm-1
(Mo-Mo X-ray Spectrum, 6cm thick breast Tissue)

|  | Fatty tissue | | 50% glandular, 50% fatty | | Glandular tissue | |
|---|---|---|---|---|---|---|
|  | No scatter | With scatter | No scatter | With scatter | No scatter | With scatter |
| 25 kVp | 0.738 | 0.659 | 0.867 | 0.787 | 1.002 | 0.923 |
| 30 kVp | 0.655 | 0.575 | 0.751 | 0.672 | 0.846 | 0.767 |
| $\Delta\mu$ | 0.083 | 0.084 | 0.116 | 0.115 | 0.156 | 0.156 |

FIG. 5

DYNAMIC EXPOSURE CONTROL IN RADIOGRAPHY

CROSS REFERENCES TO RELATED APPLICATIONS

This application claims the benefit of priority under 35 U.S.C. §119(e) from commonly owned U.S. provisional patent application Ser. No. 60/459,480, entitled "Dynamic Exposure Control in Radiography," and filed on Apr. 1, 2003, and commonly owned U.S. provisional patent application Ser. No. 60/527,236, entitled "Dynamic Exposure Control in Radiography", and filed on Dec. 5, 2003.

FIELD OF THE INVENTION

The present invention relates to exposure control in radiography.

BACKGROUND

X-ray radiography is commonly utilized to visualize a target object, for example bone or tissue. An x-ray source generates x-rays which penetrate the target object, and are transmitted therethrough. Variations in composition and thickness in different regions of the target object are revealed, as a result of the differential absorption of x-rays in the different regions.

In film-based radiography systems, the x-rays are registered on a photosensitive film placed behind the target object. The variations in the composition and thickness of the target object appear as contrasts, e.g. dark and light areas, on the film. In digital x-ray radiography systems, a digital x-ray detection system (e.g. a flat panel detector) is connected to a digital image processor, which processes the detection signals to generate digital images of the target object.

As x-rays traverse a target object, the x-ray photons undergo various interactions (e.g., absorption and scattering) with the atoms forming the target object. As a consequence, the x-rays are attenuated exponentially, according to the following formula:

$$I = I_0 e^{-\mu x},$$

where I is the intensity of x-rays that have passed through the object, $I_0$ is the intensity of x-rays before passing through the object, $\mu$ is the energy-dependent attenuation coefficient of the object at a given x-ray energy, and x is the thickness of the object.

In radiography in general, and in mammography in particular, the x-ray spectrum must be precisely controlled, in order to optimize the quality of radiographic image, as well as the diagnostic procedure for the patient. The goal is to obtain an optimal image quality for the radiograph, while subjecting the patient to the lowest possible dose. Regarding image quality, it is desirable that an x-ray radiograph provide high spatial resolution and high contrast-to-noise ratio. In film mammography, an additional requirement is that the film be properly darkened. In mammography, the tissues under examination are very similar in structure and composition, and therefore precisely controlling the x-ray exposure parameters is critical, in order to obtain an image having an adequate contrast and resolution.

At present, a known technique for optimizing the x-ray spectrum for an x-ray radiography procedure is the acquisition of a single pre-exposure at the beginning of the exposure, at a constant kVp level. The pre-exposure takes place during a time period that is short compared to the total exposure time. Information from sensors which detect pre-exposure radiation is used to adjust the x-ray exposure parameters (e.g. operating voltage, operating current, focal spot size) of the x-ray tube for the main exposure. This procedure (sometimes referred to as the "pre-pulse" method) provides better control of the parameters, as compared to other known methods in which an estimate of the thickness and density of the target object is all that is used when setting parameters such as the operating voltage and the operating current, for the entire exposure period.

The above-described "pre-pulse" procedure has a number of limitations, however, which arise from inaccuracies that occur when optimal x-ray spectra and optimal x-ray exposure parameters are predicted using a sensor signal at a single, constant kVp level. Pre-pulse sensor information at constant kVp is often unreliable, because of sensor sensitivity drift. The overall attenuation measurement result at constant kVp is strongly affected by the scattered radiation. Because of these limitations, the pre-pulse method currently known in the art does not always allow a maximum image contrast-to-noise ratio to be attained, at a minimum level of radiation dose to the patient.

It is therefore desirable to provide an x-ray exposure control technique that overcomes the limitations (described above) of currently used methods of exposure control in radiography, including mammography.

SUMMARY

The present invention is directed to a method and system for optimizing image quality in x-ray radiography while minimizing the dose to the patient, by dynamically controlling x-ray exposure parameters during radiographic imaging.

A method is provided for optimizing image quality and dose rate for an x-ray image that is produced by irradiating an object (e.g. anatomical tissue of a patient) with x-rays from an x-ray apparatus, during an x-ray exposure period. The method involves dynamic control of one or more x-ray exposure parameters, such as kVp (operating voltage), mA (tube current), soft x-ray filter parameters, and focal spot size, based on real time sensor information during the radiographic image acquisition.

In one embodiment, the method includes measuring the object tissue thickness, to determine a first kVp level and a second kVp level for the operating voltage of the x-ray apparatus. During at least a first and a second sampling interval in the beginning of the x-ray exposure period, the x-ray apparatus is operated at the first and second kVp levels, respectively. After each sampling interval, x-rays that have passed through at least a portion of object are detected in real time, using one or more sensors (preferably multiple sensors) disposed between the object and the image plane that is formed by the x-ray detectors. The sensor output signals are then processed, in order to determine the optimal value of the operating voltage, as well as the optimal values of one or more additional x-ray exposure parameters (e.g., mA, focal spot size, soft x-ray filter parameters) of the x-ray apparatus. The x-ray exposure parameters are set to these optimal values, for the remainder of the x-ray exposure period.

In one embodiment, determining the optimal values of the x-ray exposure parameters involves: 1) calculating the differential attenuation coefficient of the exposed tissue for the first and second kVp levels, using the sensor output signals and the measured thickness of the tissue; 2) creating at least one $\Delta\mu$ table for two kVp levels and various tissue compositions; and 3) using the $\Delta\mu$ table together with the determined differential attenuation coefficient to determine the composition of the tissue, and to determine the optimal values of the x-ray exposure parameters for the duration of the x-ray exposure period.

Unlike prior art techniques such as the pre-pulse method, in which x-rays are sampled during a single sampling period in the beginning of the exposure period, in the present invention x-rays are sampled during at least two sampling intervals. By using more than one sampling interval in the beginning of the procedure, the accuracy for predicting the optimal x-ray tube settings is significantly improved. This, in turn, allows for the radiographic contrast of the image of the tissue to be significantly improved, while minimizing the dose to the patient.

An x-ray apparatus is provided for generating an x-ray image of an object while dynamically controlling one or more x-ray exposure parameters during an x-ray exposure period, so as to optimize image quality and minimize the radiation dose to the patient. The x-ray apparatus includes an x-ray source for generating x-rays directed towards and through the object, and an x-ray imaging system for receiving x-rays from the x-ray source that have passed through the object, and for generating an image of the object from the received x-rays. The x-ray imaging system may be a radiographic film. Alternatively, the x-ray imaging system may include a digital radiography detector, plus an image processor.

One or more sensors (preferably multiple sensors) are provided for detecting x-rays from the x-ray source that have traversed the object during at least two sampling periods, and for generating output signals representative of the attenuated intensity of the detected x-rays. The sensors are disposed between the target object and the image plane of the object. Processing means are provided for calculating the optimal values of one or more x-ray exposure parameters using the sensor output signals. Control means, responsive to these optimal values, are provided, for setting the x-ray exposure parameters to the optimal values computed after the last sampling interval, and for maintaining said x-ray exposure parameters at these optimal values for the remainder of the x-ray exposure period.

DESCRIPTION

The present invention provides a method and system for optimizing image quality and diagnostic procedure in x-ray radiography, by dynamically controlling the incident x-ray spectrum and the x-ray exposure parameters during the initial x-ray exposure period so as to optimize image quality and minimize the dose rate to the patient.

Figure 1:
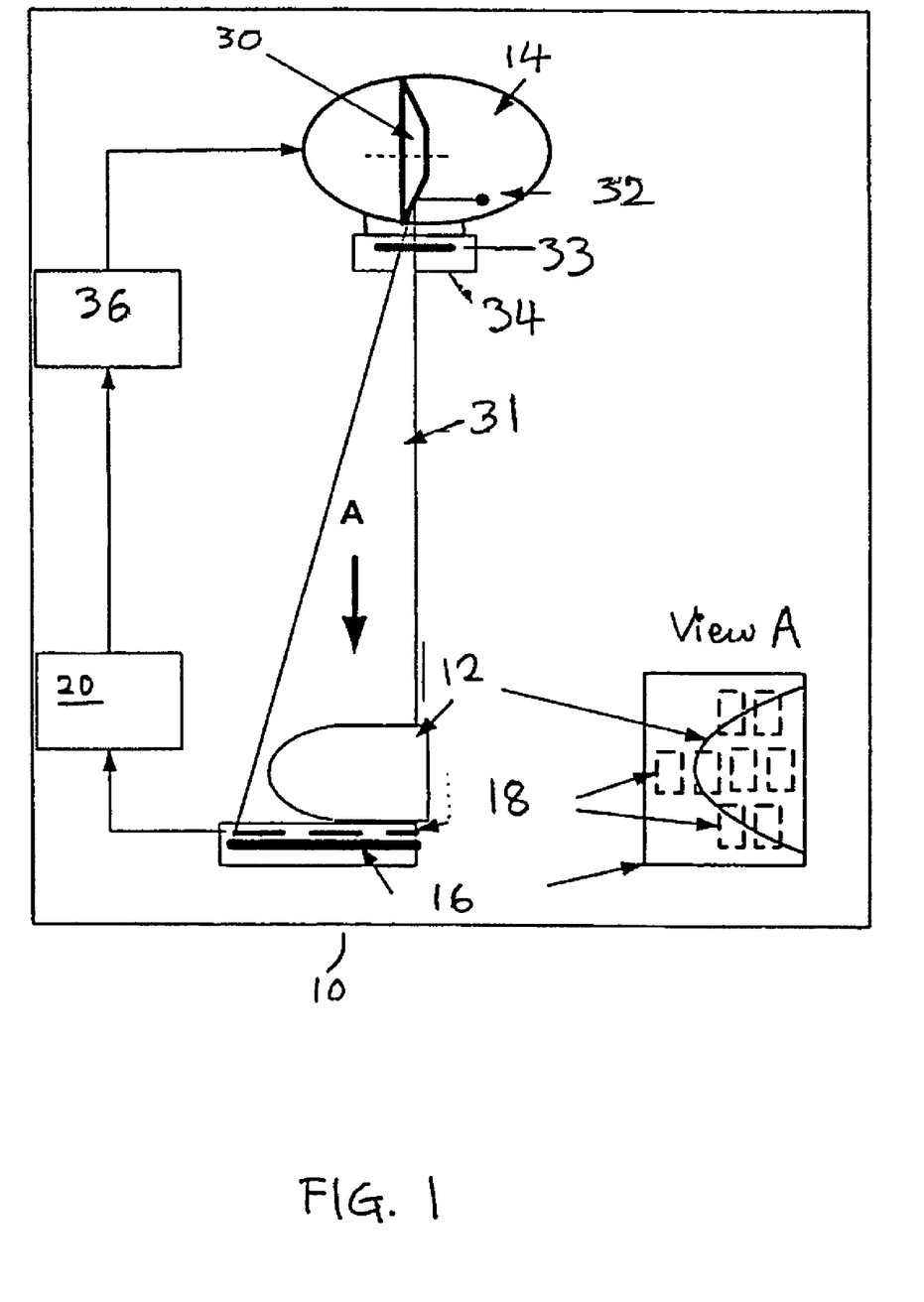
FIG. 1 illustrates a schematic block diagram of an x-ray mammography apparatus with dynamic exposure control, in accordance with one embodiment of the present invention.

FIG. 1 illustrates a schematic block diagram of an x-ray apparatus 10, constructed in accordance with one embodiment of the present invention. In overview, the apparatus 10 includes an x-ray source 14 for generating x-rays directed towards and through an object 12, an x-ray imaging system 16, one or more sensors 18, a feedback controller 20, and an x-ray controller 36. The x-ray imaging system 16 receives x-rays (emitted from the x-ray source 14) that have passed through the object 12, and generates an image of the object 12 from the received x-rays. The sensors 18 detect those x-rays from the x-ray source 14 that have passed through the object, during at least two sampling periods that are small compared to the x-ray exposure period. The sensors 18 are positioned between the object 12, and the imaging system 16. The controllers 20 and 36 are typically multi-processor computers. In medical applications (for example mammography), the object 12 consists of anatomical tissue of a patient, i.e. is a portion of the human anatomy (for example a breast in mammography applications).

Typically, the x-ray source 14 includes an x-ray emissive target 30, which emits x-rays 31 from a focal spot 32 within the target, in response to incident electrons generated by an electron source such as a cathode (not shown) within the x-ray source 14. The electrons are accelerated toward the target by an accelerating voltage, and strike the focal spot 32. The x-rays are emitted as a result of the interaction between the incident accelerated electrons and the atoms forming the target 30. The focal spot 32 is the area within the x-ray target 30 that is struck by the incident electrons, and from which x-rays 31 are emitted. The kVp of the x-ray source 14, i.e. the x-ray source operating voltage, provides the accelerating voltage for accelerating the electrons from the electron source towards the x-ray emissive target 30. The x-ray target 30 is made of one or more x-ray emissive materials, including but not limited to tungsten, molybdenum, and/or rhodium, by way of example. One or more soft x-ray filters 33 may be placed between the x-ray source 14 and the x-ray imaging system 16. The soft x-ray filters absorb most of the soft x-rays (i.e. low energy x-rays) within the incident x-ray spectrum. A collimator 34 is also usually provided, in order to produce a collimated x-ray beam.

In film-based x-ray radiography, the x-ray imaging system 16 is typically an image receptor, for example a photographic film 16 in the embodiment illustrated in FIG. 1. Usually the film or receptor is substantially planar, defining an image plane. One or more intensifying screens (not shown) may be used with the photosensitive x-ray film, in order to intensify the effect of x-rays during the exposure of the x-ray film. Typically, the photosensitive x-ray film 16 consists of a radiation sensitive emulsion (composed of small crystal grains of a silver halide, for example), coated on one or both sides of a base. The exposure of the x-ray film 16 by light or x-rays reduces the silver ions in the emulsion to metallic silver atoms. The blackening of the film 16 is caused by the formation of metallic (black) silver in the emulsion. One of the conditions that need to be satisfied for purposes of optimal image quality and dose rate to patient, is that the photosensitive film be properly darkened, without requiring excessive exposure time.

In an alternative embodiment of the invention, the x-ray imaging system 16 may include: 1) a digital x-ray radiography system, plus 2) an image processor (not shown). For example, in one embodiment, a digital x-ray radiography system can be a flat panel detector. The signals generated by the detectors are sent to the digital image processor, which digitally processes the signals to generate digital images of the target object.

The characteristics of the x-ray radiation spectrum emitted from the x-ray source 14 are determined by a number of x-ray exposure parameters, which affect x-ray image quality. The x-ray exposure parameters that need to be adjusted in order to optimize image quality include, but are not limited to: x-ray tube operating voltage (kVp), operating current, focal spot size, and number and type of soft x-ray filters. The x-ray controller 36 controls and adjusts these x-ray exposure parameters, i.e. the settings for the x-ray apparatus 10, so that an optimal image quality and dose rate can be achieved. For example, a higher operating voltage (i.e. kVp) produces higher energy x-rays, which pass through imaged tissue more easily without being absorbed. A lower operating voltage produces lower energy x-ray photons, which are more readily absorbed by imaged tissue. The operating current is the current formed by the electrons that impinge upon the x-ray target 30, causing emission of x-rays. The flux of x-ray photons emitted from the target 30 is proportional to the operating current. For a given operating voltage, increasing the operating current results in a higher optical density of exposed film, or higher signal in digital radiography detector.

In the present invention, the sensor(s) 18 detect x-rays that have passed through the object 12 during at least two sampling periods. Typically, the sampling periods are very short, compared to the x-ray exposure period during which the object 12 is exposed to x-rays 31 from the x-ray source 14. The sensors 18 generate output signals representative of the attenuated intensity of the detected x-rays. In one system known and described in the prior art, the sensor(s) are placed underneath the film (i.e. below the image plane), and detects radiation that has passed through the object 12 as well as the film 16. The sensor(s) used in the prior art therefore generate signals that are proportional to the rate of darkening of the film. In contrast, in the embodiment illustrated in FIG. 1, the sensors 18 are ionization chambers that are sufficiently transparent to the x-rays, and are located between the object 12 and the image plane defined by the film 16, i.e. between the object 12 and the x-ray imaging system 16. Therefore, the sensors 18 do not detect x-rays after they pass through the film 16 (or other type of x-ray image receptor 16), but rather detect them before they reach the film 16. One advantage of such a location is that it can be used with digital detectors, which totally block the x-rays. The insert in FIG. 1, labeled "view A," illustrates the location of the sensors 18 along a direction A, indicated in FIG. 1 by an arrow.

Figure 2:
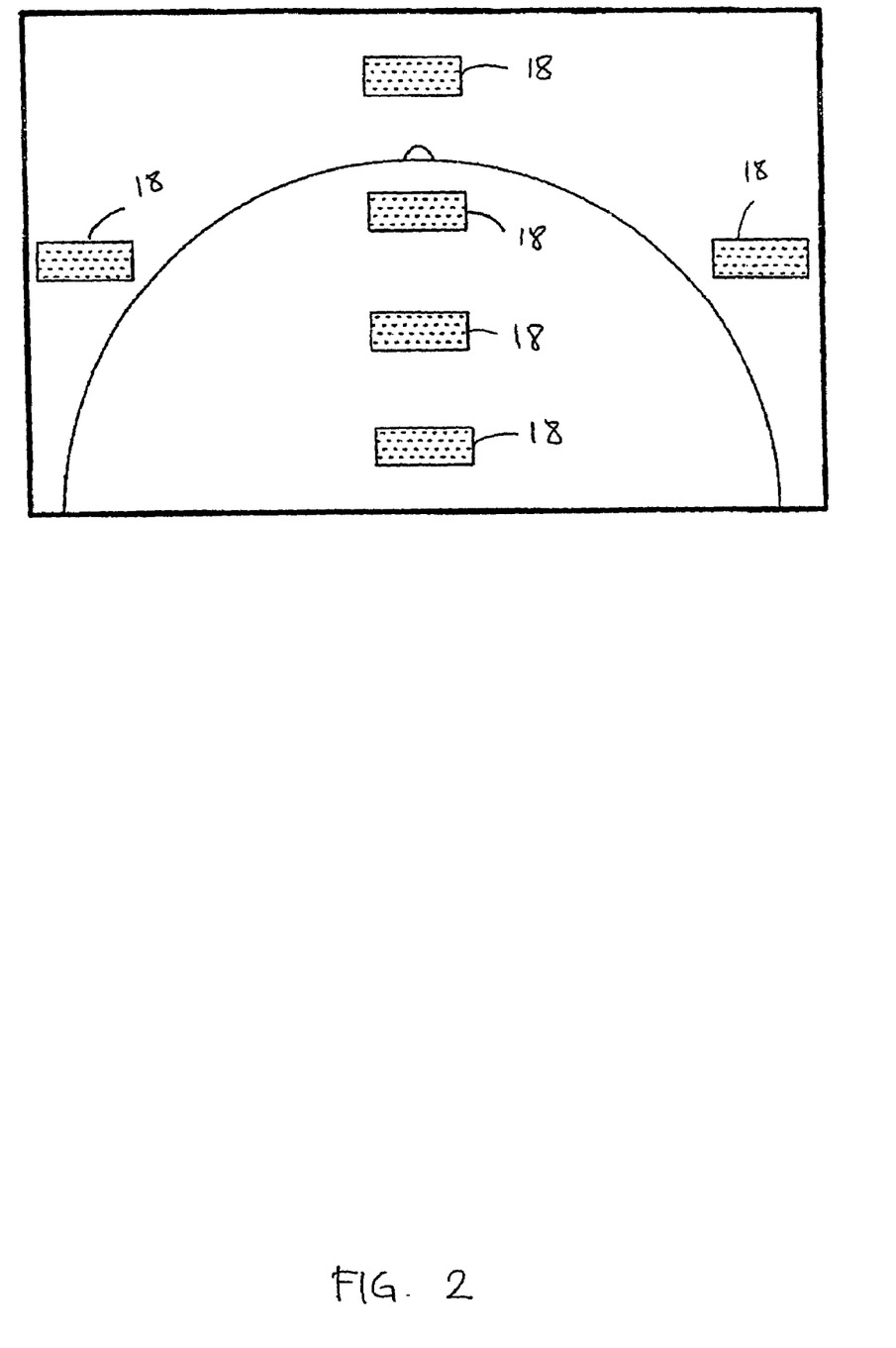
FIG. 2 illustrates an example of the locations of multiple sensors in the image plane of the target object.

Preferably, a plurality of sensors are used in the present invention, so that the output signals from multiple x-ray sensors (as opposed to signals from a single sensor) are monitored. FIG. 2 illustrates an example of the locations of multiple sensors 18 in the image plane of the target object. The plurality of sensors 18 are disposed between the object 12 and the x-ray film 16.

For optimal utilization of the technique of the present invention in mammography, it is beneficial to monitor the x-rays that impinge upon several different areas of the target object (i.e. the breast), as well as outside the area of the breast. In this way, multiple values of the attenuation coefficient can be produced, for different areas of the object, for example for different breast areas in mammography. By producing multiple attenuation coefficients for multiple areas of the object, the image quality can be optimized for the area of interest. This is in contrast to the system described in the prior art, for example in U.S. Pat. No. Re. 33,634 to Yanaki, in which only one sensor is used for detecting the radiation that passed through tissue. While another sensor may be used in the system described in the Yanaki patent, the other sensor is only used for calibration purposes, and is only for detecting radiation that has not passed through the tissue. Accordingly, in the Yanaki patent, only one value for the attenuation coefficient is derived, and that single value is used to optimize the main exposure conditions.

In the present invention, the use of multiple sensors, as illustrated in FIG. 2, enables the automatic selection of the area of interest within the object (e.g. breast), using a microprocessor. In contrast, in the Yanaki patent, and in other methods known in the art, a technician manually positions the sensor(s) in the area of interest. This is a subjective procedure, and requires highly experienced and well-trained personnel for operating the apparatus. The advantage of using multiple sensors, as in the embodiment illustrated in FIG. 2, is that intervention by trained personnel is no longer necessary.

The output signals from the plurality of sensors 18 are processed, in the beginning of the x-ray exposure period, in order to determine a set of optimal values for one or more x-ray exposure parameters. In the pre-pulse method known in the art, sensor information obtained from a single pre-exposure sampling period is used to determine these optimum values. In contrast, in the present invention sensor information obtained from at least two sampling periods is used to predict (using algorithms known in the art) the optimal x-ray tube settings for the remainder of the x-ray exposure period.

Figure 3:
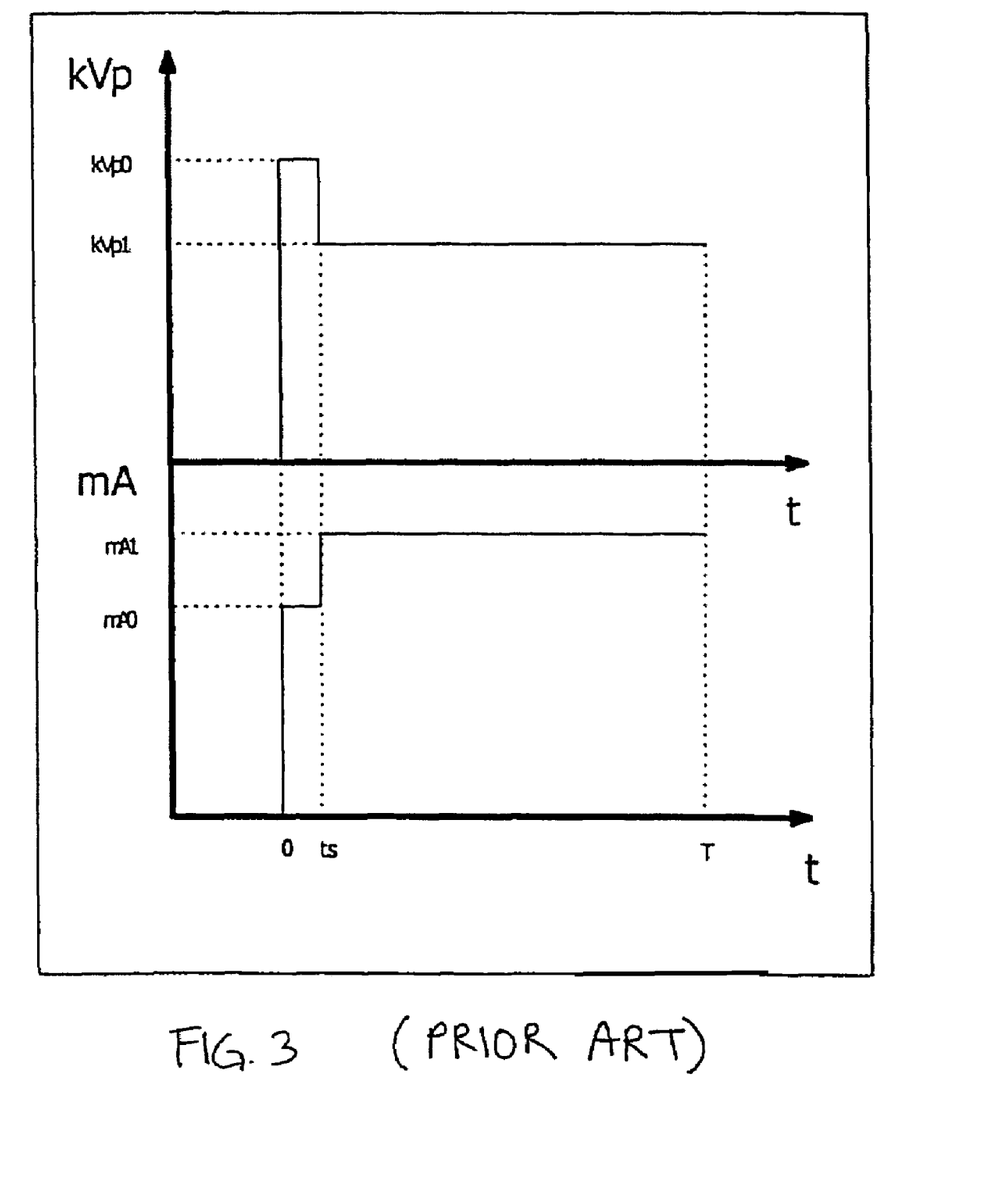
FIG. 3 illustrates an example of the kVp(t) function, i.e. the variation of the tube voltage (kVp) as a function of time, in a pre-pulse method known in the art.

FIG. 3 illustrates the kVp(t) function, i.e. the variation of the x-ray source operating voltage (kVp) as a function of time, in a pre-pulse method known in the art, for example the pre-pulse procedure disclosed in the Yanaki patent in connection with a mammography apparatus. In the pre-pulse method, the thickness of the breast tissue is measured, and a single set of initial x-ray tube settings is determined. The x-ray machine is operated, at these initial settings, for a single sampling interval (i.e. "pre-exposure"). The sampling interval is small, compared to the duration of the entire x-ray exposure.

Based on the measured tissue thickness, $\mu$-tables, and information obtained from the sensor during the pre-exposure, a microprocessor determines the attenuation coefficient of the tissue, exposed at a single energy level, and determines the optimum x-ray settings. As mentioned earlier, these x-ray settings include x-ray tube operating voltage (kVp), operating current, focal spot size, and number and type of soft x-ray filters. The x-ray apparatus continues to be operated at these optimal settings, until optimum visualization is achieved. In the pre-pulse method, exposure time control is performed using the sensor. FIG. 3 illustrates the sequence of the operating high voltages, and the x-ray tube currents. FIG. 3 also shows that in the pre-pulse method, the sampling process is by changing just once the kVp (x-ray source operating voltage) and the mA (x-ray current), after a small sampling interval $t_s$, then maintaining the kVp and the mA constant until time T, at which optimal visualization (or film exposure) is achieved. The sampling time $t_s$ is much less than the time T required for achieving optimal visualization and film exposure.

The optimal x-ray exposure parameters are those that provide optimal image quality, i.e. optimum film darkness, optimum contrast-to-noise ratio, at fixed dose to the patient. In order to determine the optimized x-ray exposure parameters, it is preferable to obtain more than one sample of x-ray data from the object in the beginning of the x-ray exposure, each at a different value of kVp. such dual, or multiple energy measurement allows for better accuracy in predicting the optimal x-ray exposure conditions, such as kVp, mA, focal spot size, and soft x-ray filter combination.

Accordingly, in a preferred embodiment the method of the present invention includes taking at least two samples of data during at least two consecutive sampling intervals $\Delta t_1$ and $\Delta t_2$, in the beginning of the exposure period. This dual energy information is used to define the dynamic control of the high voltage and current of the x-ray source, as well as the size of the focal spot, and the soft x-ray filter parameters. In the present invention, it is recognized that prediction of the optimal x-ray tube settings based on a single sampling of the sensor at one energy level is not very accurate, primarily due to the errors introduced by the scattered radiation, and sensor drift, and can be significantly improved by using more than one sampling intervals (at respective different energy levels) in the beginning of the procedure. This in turn improves the contrast of the radiographic image for given dose to the patient.

In other embodiments, more than two sampling intervals may be used for the pre-exposure, each at different kVp levels. In these embodiments, the x-ray apparatus may be operated during n sampling intervals $\Delta t_1^1, \Delta t_1^2, \ldots, \Delta t_1^n$ during the pre-exposure, at kVp levels $kVp_1^1, kVp_1^2, \ldots kVp_1^n$, respectively. In this case the tissue composition may be determined more accurately based on multiple measured differential attenuation coefficients.

Using dual (or multiple) energy information from the same sensor under the breast provides a better prediction of the scatter intensity at different kVp levels, as compared to using two sensors (one in the breast area and another outside the breast area) at constant kVp, as is done in the prior art. Having dual (or multiple) energy information in the beginning of the exposure reduces the effects of the sensor sensitivity drift after calibration. This improves the accuracy of the prediction of the exposure conditions, as compared to the accuracy achieved in the pre-pulse method known in the art in which a constant kVp is used. Finally, using multiple sensors at dual (or multiple) energies of x-rays allows the x-ray spectra to be tailored to various tissue compositions within the breast.

The inaccuracy of predicting the optimal settings based on one sensor sampling interval arises from the fact that the measurement of x-ray attenuation coefficient by the sensor is affected by the scattered x-ray radiation. As known in the art (and described for example in the Yanaki patent), the sensor signal when the tissue is present is expressed as follows:

$$i = i_0 \cdot e^{-\mu x} \quad (1)$$

where $i_0$ is the sensor current when the tissue is not present, $\mu$ is the linear x-ray attenuation coefficient of the tissue, and x is the thickness of the tissue. Equation (1), as well as equations (2)-(9) below, are valid for monochromatic x-rays only, and are provided for purposes of describing the relation between the attenuation coefficient, tissue thickness, and desired x-ray parameters.

From equation (1), the attenuation coefficient can be expressed as follows:

$$\mu = \frac{1}{x} \cdot \ln\left(\frac{i_0}{i}\right) \quad (2)$$

However, this expression is only an approximation, because it does not include the contribution of radiation scattered from the tissue and from other elements of the x-ray apparatus in the path of the x-rays. The complete expression for the sensor signal is given by:

$$i = i_0 \cdot e^{-\mu x} + i_{sc} \quad (3)$$

The contribution of the scattered radiation is difficult to estimate or calibrate, during clinical conditions, because it depends on the size of the tissue sample (i.e. the breast diameter and thickness), its position with respect to the imaging plane and the focal spot, as well as on the use and quality of the grids, and on the magnification techniques. The scattered radiation can be characterized by the scatter-to-primary ratio ("SPR"). Using this characterization, the expression (2) can be rewritten as:

$$i = i_0 \cdot (1 + SPR) \cdot e^{-\mu x}, \quad (4)$$

and the attenuation coefficient $\mu$, measured in the prior art using just one sampling interval, becomes:

$$\mu = \frac{1}{x} \cdot \ln\left[\frac{i_0}{i} \cdot (1 + SPR)\right]. \quad (5)$$

A comparison between equation (1) and equation (2) shows that the measurement error is:

$$\delta\mu = \frac{1}{x} \cdot \ln(1 + SPR) \quad (6)$$

For a mammography apparatus at an x-ray tube operating voltage of 30 kVp, the SPR for a 6 cm thick BR-12 phantom without an antiscatter grid is 0.908, while the SPR with the grid is 0.26. This means that the errors in the attenuation coefficient that have been encountered in the prior art are 0.108 cm$^{-1}$, and 0.039 cm$^{-1}$, respectively. The role of grids is presently being reevaluated for digital mammography, because it is beneficial in many clinical cases to operate without grids. It is therefore necessary that mammography systems, and the pre-exposure method, produce accurate results without the use of the grids.

Typically, the attenuation coefficient for different types of breast tissues at 20 keV varies from about 0.50 cm$^{-1}$ to about 0.77 cm$^{-1}$. Therefore, an error of 0.108 cm$^{-1}$ does not allow an accurate determination of the composition of breast tissue, because the error covers approximately 40% of the possible variation in breast tissue.

In the present invention, at least two samples of the sensor signals are acquired, using at least two different x-ray tube operating voltages, to produce at least two values of attenuation coefficients. In the embodiment in which two values of attenuation coefficients are produced, the following expressions hold:

$$\mu_1 = \frac{1}{x} \cdot \ln\left[\frac{i_{01}}{i_1} \cdot (1 + SPR)\right], \quad (7)$$

and $$\mu_2 = \frac{1}{x} \cdot \ln\left[\frac{i_{02}}{i_2} \cdot (1 + SPR)\right]. \quad (8)$$

The difference between the two values $\mu_1$ and $\mu_2$, i.e. the differential attenuation coefficient $\Delta\mu = \mu_1 - \mu_2$, is almost independent of the amount of scattered radiation, and therefore serves as a measure of the tissue density:

$$\Delta\mu = \mu_2 - \mu_1 = \frac{1}{x} \cdot \ln\left(\frac{i_{02} \cdot i_1}{i_2 \cdot i_{01}}\right) \quad (9)$$

The expression for the differential attenuation coefficient given by equation (9) is an approximation that disregards an error due to the kVp dependence of SPR. However, it has been found (e.g. by Boone et al.) that the energy dependence of SPR is very weak, and that the error in the differential attenuation coefficient due to this dependence is negligibly small. According to one set of data (taken by Boone et al.), the estimated error in $\Delta\mu$ for a Mo/Mo x-ray spectrum is 0.0025 cm-1 for a 6 cm breast and a high voltage change from 25 kVp to 30 kVp.

Figure 4:
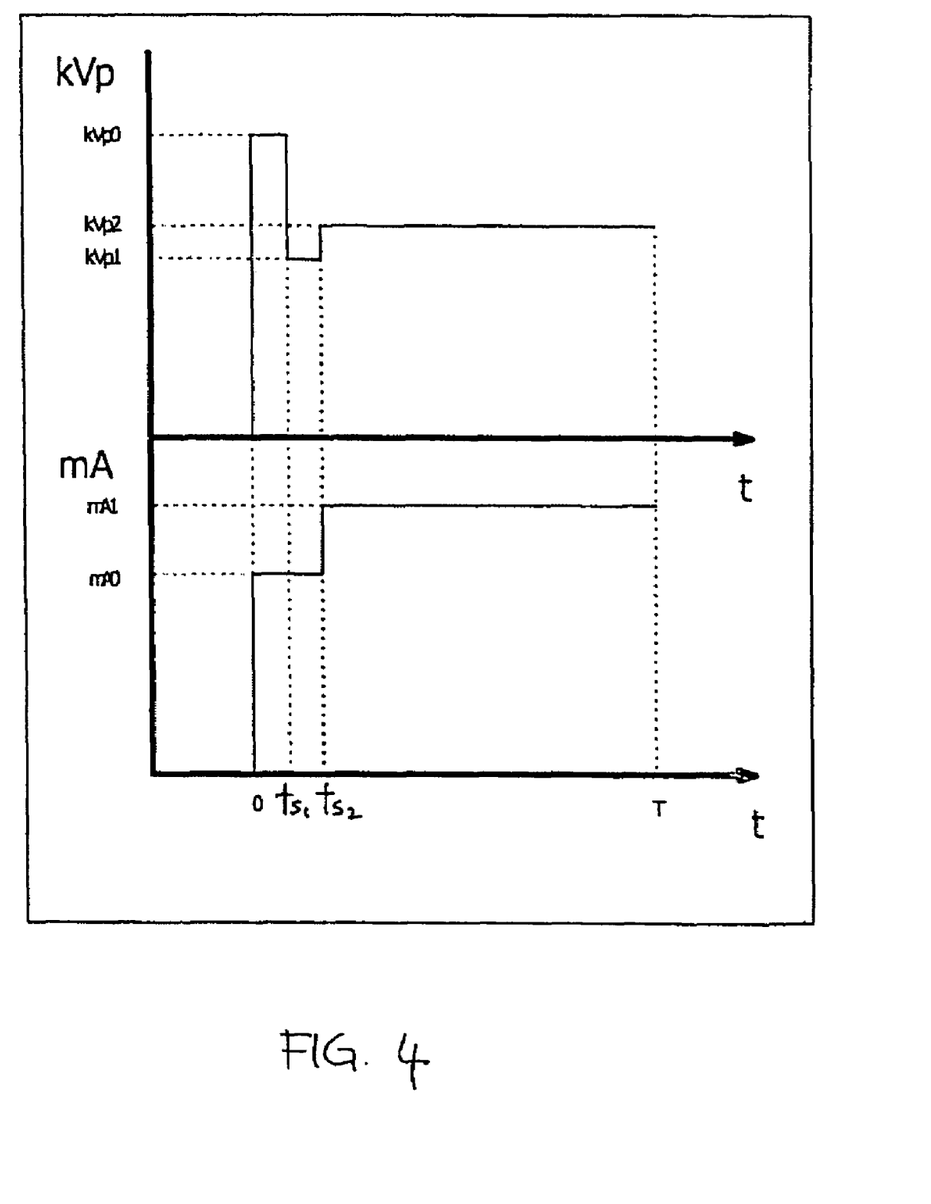
FIG. 4 illustrates an example of the kVp(t) function, in a dual-energy pre-exposure method in accordance with one embodiment of the present invention.

FIG. 4 schematically illustrates the dual energy pre-exposure method in accordance with one embodiment of the present invention, as performed using the apparatus illustrated in FIG. 1. In the illustrated method, two sampling intervals $\Delta t_1 = t_{s1}$, and $\Delta t_2 = t_{s1} - t_{s2}$ ($t_{s2} \ll T$) are used to predict the x-ray apparatus settings for the remainder of the exposure period. As a first step, the thickness of the tissue 12 is measured. Based on the measured thickness of the tissue 12, two kVp levels are determined, as well as an initial setting for the tube current, focal spot size, and filter for the pre-exposure. The x-ray apparatus 10 is then operated at each of the two initial settings, during the two small sampling intervals $\Delta t_1$ and $\Delta t_2$.

The feedback controller 20 then processes the output signals from the sensors 18, together with the measured thickness of the tissue, to calculate the differential attenuation coefficient $\Delta\mu$ of the exposed tissue 12 at two energy levels. The feedback controller 20 then computes the tissue composition by comparing the $\Delta\mu$ value with the table of $\Delta\mu$ coefficients which is obtained using calibration. The $\Delta\mu$ calibration table consists of $\Delta\mu$ values for preferably at least three tissue compositions, for different tissue thickness values. For example in mammography the table contains values for 100% fatty, 50% fatty+50% glandular, and 100% glandular tissue, for breast thickness from 1 to 9 cm. The optimal x-ray exposure parameters can then be determined using the known relationships between the tissue composition and the optimal x-ray exposure conditions, which maximize the diagnostic value of the procedure, at low dose to the patient. The feedback controller 20 passes on the optimum x-ray settings to the x-ray controller 36, which adjusts the x-ray exposure parameters to these optimum settings.

FIG. 4 shows that in the dual energy method of the present invention, the kVp level changes from the initial value, $kVp_0$, to the value $kVp_1$ at the end of the first sampling interval $t_{s1}$, then to the final optimized value $kVp_2$. The kVp change from $kVp_0$ to $kVp_1$ is computed based on the sensor feedback at the end of $t_{s1}$ (together with the measured tissue thickness). The kVp change from $kVp_1$ to $kVp_2$ is based on the sensor feedback during two sampling intervals (together with the measured tissue thickness). The tube current mA, as well as the focal spot size and the x-ray filter parameters, are changed after the optimal kVp setting kVp2 is achieved. The x-ray controller 36 changes the operating voltage, tube current, focal spot size, and x-ray filter parameters to these optimum settings computed by the feedback controller 20. The x-ray controller 36 continues to operate the x-ray apparatus 10 at these optimal settings, until a time T at which optimum visualization is achieved.

Figure 5:
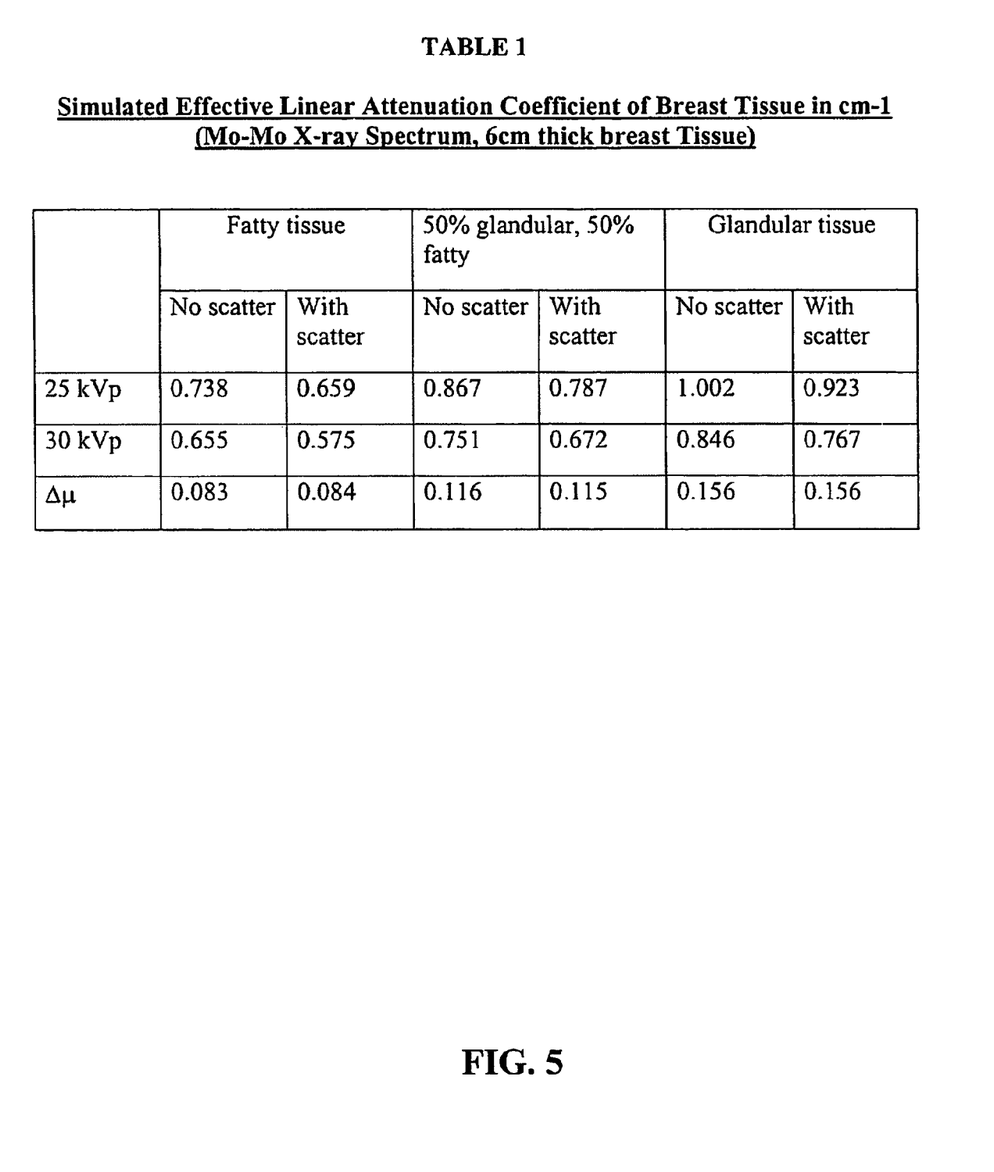
FIG. 5 provides a table ("Table 1") illustrating an example of the differential attenuation coefficient values simulation for polychromatic Mo—Mo— x-ray spectra, at 25 kVp and at 30 kVp respectively, for a 6 cm thick breast tissue.

FIG. 5 provides a table ("Table 1") illustrating an example of the differential attenuation coefficient values simulation for polychromatic Mo—Mo— x-ray spectra, at 25 kVp, and at 30 kVp, respectively. The simulation in Table 1 is done for a 6 cm thick breast tissue, with a semi-circular diameter of 15 cm. The simulations were performed for the following breast tissue compositions: 1) 100% fatty tissue; 2) 50% glandular tissue+50% fatty tissue; and 3) 100% glandular tissue. Two values of the attenuation coefficient, with and without scatter, are calculated, in order to show the uncertainty in the measurement due to scattered radiation. While the linear attenuation coefficient is strongly affected by the scattered radiation, the differential coefficient $\Delta\mu$ remains practically constant. The error in $\Delta\mu$ does not exceed 0.0025 cm$^{-1}$, for a 5 kVp change in the x-ray tube operating voltage, which is consistent with the discussion in paragraph [0045].

As can be seen from Table 1 in FIG 5 the improved accuracy of the method of the present invention is striking, for the case of two kVp values (at 25 kVp, and 30 kVp, respectively). In the prior art, which uses one kVp value 30 kVp in pre-exposure, the error in terms of the percentage of the glandular tissue equals to about 41.3%. This value is computed as follows: $\{(0.751-0.672)/(0.846-0.655)\}*100\%=41.3\%$. In the method of the present invention, in which a dual energy re-exposure is performed and $\Delta\mu$ tables are used, the error is much smaller, namely 3.4%. In other words, the error is reduced by a factor of more than about 10. The error in the dual energy pre-exposure method of the present invention is computed as follows: $\{0.0025/(0.156-0.083)\}*100\%=3.4\%$.

In a preferred embodiment of the invention, at least one $\Delta\mu$ table is created, for every centimeter of the breast tissue. Every table defines two kVp values for the pre-exposure, and at least three $\Delta\mu$ values for at least three breast tissue compositions. Based on these tables and based on the measured $\Delta\mu$ value, the tissue composition is determined. The known tissue composition allows the optimum x-ray settings (primarily kVp) to be chosen for the rest of the exposure period, using algorithms known in the art. An accurate measurement of the tissue composition allows a more accurate prediction of the exposure time to be made, which in turn makes it unnecessary to control the exposure time using a sensor, as is done in the prior art. This is especially advantageous for digital systems, in which accurate synchronization of the x-rays with the detector integration cycle is very important.

The technique of the present invention provides a level of x-ray control that has not been obtained previously. Because the x-rays are sampled at more than one sampling intervals, rather than during a single sampling period at the beginning of the exposure period, the method and system of the present invention avoids the problems that are encountered in the pre-pulse method and that relate to sensor sensitivity drift and the change in the intensity of scatter radiation.

In sum, the method and system of the present invention provide a number of advantages over the known art. The improved accuracy in determining the tissue composition during the pre-exposure allows the radiographic contrast of the diagnostic image (in both film-based radiography and digital radiography systems) to be significantly improved, while minimizing the dose to the patient. Further, in the case of digital systems, the improved accuracy in determining of the x-ray tube settings allows improving the synchronization of the x-rays with the digital detectors, while maintaining optimum exposure.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for optimizing radiographic image quality of a single x-ray image of an object that is produced by irradiating the object with x-rays from an x-ray apparatus during an x-ray exposure period, the x-ray apparatus including an x-ray source configured to generate x-rays directed towards and through said object and an x-ray imaging system configured to receive x-rays that have been emitted from the x-ray source and have passed through the object, the x-ray source including an electron source and an x-ray emissive target, the method comprising:

A. determining a first operating voltage level $kVp_0$ of the x-ray source for initial operation of the x-ray apparatus;

B. during a first sampling interval $\Delta t_1$ in the beginning of the x-ray exposure period, operating the x-ray source in the x-ray apparatus at said first operating voltage level $kVp_0$ and using one or more sensors to detect x-rays that have passed through a portion of the object during the interval $\Delta t_1$, the one or more sensors disposed between the object and the x-ray imaging system, wherein the first sampling interval $\Delta t_1$ is relatively small compared to the x-ray exposure period, wherein the x-ray exposure period is a length of time during which said object must be irradiated with the x-rays in order for said single x-ray image of said object to be generated;

C. after said first sampling interval $\Delta t_1$, processing the output signals from said sensors to determine a second operating voltage level $kVp_1$ of the x-ray source;

D. during a second sampling interval $\Delta t_2$ within the same x-ray exposure period, wherein the object is irradiated with x-rays from the x-ray apparatus during said x-ray exposure period to generate said single image of the object, operating the x-ray source of said x-ray apparatus at said second operating voltage level $kVp_1$ and using said sensors to detect x-rays that have passed through a portion of the object during the interval $\Delta t_2$, wherein the second sampling interval $\Delta t_2$ is also relatively small compared to the x-ray exposure period for said single image of the object; and E. after said second sampling interval $\Delta t_2$, processing the sensor output signals to determine an optimal value $kVp_2$ for the operating voltage level, and setting the operating voltage level of the x-ray source of the x-ray apparatus to said optimal value $kVp_2$ for the remainder of the x-ray exposure period of the single image of the entire object.

2. A method in accordance with claim 1, further comprising: determining the optimal values of one or more additional x-ray exposure parameters of the x-ray apparatus, and setting said additional x-ray exposure parameters to said optimal values for the remainder of the x-ray exposure period.

3. A method in accordance with claim 2, wherein said additional x-ray exposure parameters comprise at least one of: x-ray tube current (mA), size of focal spot, and number and type of soft x-ray filters; and wherein said x-ray tube current is the current formed by electrons emitted from said electron source, said focal spot is the area within said target upon which the electrons impinge, and said soft x-ray filters are filters for absorbing soft x-ray radiation.

4. A method in accordance with claim 2, wherein determining said optimal values of said additional x-ray parameters comprises:

A. calculating the differential attenuation coefficient $\Delta\mu$ of the exposed tissue at said voltage level $kVp_1$, based on the output signals from said sensors, and based on the measured thickness of said tissue;

B. creating at least one $\Delta\mu$ table for at least one region of said object;

C. determining the composition of said tissue using said calculated value of $\Delta\mu$, and said at least one $\Delta\mu$ table; and D. determining said optimal values of said additional x-ray parameters using said tissue composition and said $\Delta\mu$ table.

5. A method in accordance with claim 1, wherein said object comprises anatomical tissue of a patient, and wherein said optimal value of said operating voltage are chosen so that the patient's exposure to x-rays is substantially minimized when the x-ray apparatus is operated at said optimal value.

6. A method in accordance with claim 1, further comprising an x-ray imaging system, and wherein said x-ray imaging system comprises one of: a) a radiographic film defining an image plane; and b) a flat panel detector configured to detect x-rays that have passed through said object, said flat panel detector being disposed along an image plane.

7. A method in accordance with claim 6, wherein said one or more sensors are positioned between said object and said image plane.

8. A method in accordance with claim 7, wherein a plurality of sensors are used to detect x-rays during said first and second sampling intervals, and wherein each of said plurality of sensors are positioned at different locations so that said sensors can detect x-rays that have traversed different portions of said object.

9. A method in accordance with claim 1, wherein said object comprises anatomical tissue of a patient, and further comprising the step of measuring the thickness of said tissue before the step of determining said first and second operating voltage levels.

10. A method in accordance with claim 9, wherein the step of determining said optimal value of said operating voltage level comprises:

A. calculating the differential attenuation coefficient $\Delta\mu$ of the exposed tissue at said voltage level $kVp_1$, based on the output signals from said sensors, and based on the measured thickness of said tissue;

B. creating at least one $\Delta\mu$ table for at least one region of said object;

C. determining the composition of said tissue using said calculated value of $\Delta\mu$, and said at least one $\Delta\mu$ table; and D. determining said optimal value of said operating voltage level, using said tissue composition and said $\Delta\mu$ table.

11. A method in accordance with claim 10, wherein at least one $\Delta\mu$ table is created in step B for every centimeter of breast tissue, and wherein each of said at least one $\Delta\mu$ table defines at least two kVp values for said sampling intervals, and at least three $\Delta\mu$ values for at least three breast tissue compositions.

12. A method in accordance with claim 1, wherein steps B and C are repeated for a plurality of n sampling intervals $\Delta t_1^1, \ldots, \Delta t_1^n$, during which the x-ray apparatus is operated at corresponding operating voltage levels $kVp_1^1, \ldots kVp_1^n$, so that said optimal operating voltage level $kVp_2$ is determined based on sensor output signals generated while the x-ray apparatus was operated at voltage level $kVp_1^n$ during a sampling interval $\Delta t_1^n$.

13. An x-ray imaging apparatus, the x-ray imaging apparatus comprising:

an x-ray source adapted to generate x-rays directed towards and through an object, the x-ray source including an electron source configured to emit electrons, and an x-ray emissive target configured to emit x-rays from a focal spot within the target in response to incident electrons that have been accelerated from said electron source toward said target at an operating voltage of said x-ray source;

an x-ray imaging system configured to receive x-rays that have been emitted from said x-ray source and that have passed through said object, and to generate an image of said object from the received x-rays;

one or more sensors disposed between the object and said x-ray imaging system, said sensors being configured to detect x-rays from said x-ray source that have traversed said object during a first sampling period $\Delta t_1$ and a second sampling period $\Delta t_2$, and to generate one or more output signals representative of the attenuated intensity of the detected x-rays, wherein the first sampling period and the second sampling period are each relatively small compared to the total exposure time during which said object is exposed to radiation generated by said x-ray source;

a processor configured to determine a first operating voltage level $kVp_0$ of the x-ray source for an initial operation of said x-ray apparatus during said first sampling period $\Delta t_1$, said processor being further configured to calculate, after said first sampling period $\Delta t_1$, a second operating voltage level $kVp_1$ of the x-ray source by processing the output signals generated by said sensors during said first sampling period, said processor being further configured to calculate, after said second sampling period $\Delta t_2$, an optimal operating voltage level $kVp_2$ of the x-ray source by processing the output signals generated by said sensors during said second sampling period; and a controller configured to adjust the operating voltage of said x-ray source to said first and second operating voltage levels during said first and second sampling periods, respectively, said controller being further configured to adjust, after said second sampling period $\Delta t_2$, the operating voltage of said x-ray source to said optimal voltage level $kVp_2$ for the remainder of said x-ray exposure period.

14. An x-ray apparatus in accordance with claim 13, wherein said processor is further configured to determine the optimal values of one or more x-ray exposure parameters, and wherein said x-ray exposure parameters include at least one of current (mA), and size of focal spot; and wherein the current is formed by said electrons emitted from said electron source.

15. An x-ray apparatus in accordance with claim 13, wherein said x-ray imaging system comprises one of: a) a radiographic film defining an image plane; and b) a flat panel detector disposed along an image plane and configured to detect x-rays that have passed through the object.

16. An x-ray apparatus in accordance with claim 13, wherein said one or more sensors comprise at least one of: an ionization chamber; a scintillator; and a solid state detector.

17. An x-ray apparatus in accordance with claim 13, wherein the object comprises anatomical tissue, and wherein said processor comprises:
  A. means for calculating the thickness of the object;
  B. means for calculating the differential attenuation coefficient of the tissue at each of said first and second kVp levels based on the output signals from said sensors and based on the measured thickness of said tissue;
  C. means for providing at least one $\Delta\mu$ table for at least one region of said object; and
  D. means for computing said optimal values of said x-ray exposure parameters using said $\Delta\mu$ table.

* * * * *